United States Patent
Kashiwabara

(10) Patent No.: US 9,461,274 B2
(45) Date of Patent: Oct. 4, 2016

(54) ORGANIC LIGHT EMITTING DEVICE AND DISPLAY UNIT

(71) Applicant: Sony Corporation, Tokyo (JP)

(72) Inventor: Mitsuhiro Kashiwabara, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 56 days.

(21) Appl. No.: 14/612,984

(22) Filed: Feb. 3, 2015

(65) Prior Publication Data

US 2015/0144936 A1  May 28, 2015

Related U.S. Application Data

(63) Continuation of application No. 11/828,746, filed on Jul. 26, 2007, now Pat. No. 9,093,664.

(30) Foreign Application Priority Data

Jul. 31, 2006  (JP) ................. 2006-208051

(51) Int. Cl.

| H01L 51/54 | (2006.01) |
|---|---|
| H01L 51/52 | (2006.01) |
| H01L 51/50 | (2006.01) |
| H01L 27/32 | (2006.01) |
| H01L 51/00 | (2006.01) |
| C07D 241/38 | (2006.01) |

(52) U.S. Cl.
CPC ....... *H01L 51/5265* (2013.01); *H01L 27/3244* (2013.01); *H01L 51/5088* (2013.01); *H01L 51/5092* (2013.01); *H01L 51/5206* (2013.01); *H01L 51/5221* (2013.01); *H01L 51/5271* (2013.01); *C07D 241/38* (2013.01); *H01L 51/0072* (2013.01)

(58) Field of Classification Search
None
See application file for complete search history.

(56) References Cited

U.S. PATENT DOCUMENTS

| 5,677,572 A | 10/1997 | Hung et al. |
|---|---|---|
| 6,366,017 B1 | 4/2002 | Antoniadis et al. |
| 7,049,741 B2 | 5/2006 | Madathil et al. |
| 2002/0158242 A1 | 10/2002 | Son et al. |
| 2002/0185969 A1 | 12/2002 | Raychaudhuri et al. |
| 2003/0035978 A1 | 2/2003 | Raychaudhuri et al. |
| 2003/0104244 A1* | 6/2003 | Aziz ............ H01L 51/5012 428/690 |
| 2003/0230980 A1 | 12/2003 | Forrest et al. |
| 2003/0232215 A1 | 12/2003 | Richter et al. |
| 2004/0086743 A1 | 5/2004 | Brown et al. |
| 2004/0113547 A1 | 6/2004 | Son et al. |
| 2004/0140758 A1 | 7/2004 | Raychaudhuri et al. |
| 2005/0208330 A1 | 9/2005 | Raychaudhuri et al. |
| 2006/0006792 A1 | 1/2006 | Strip |
| 2006/0134458 A1 | 6/2006 | Kawamura |
| 2006/0158105 A1 | 7/2006 | Kim et al. |

FOREIGN PATENT DOCUMENTS

| JP | 10-177896 | 6/1998 |
|---|---|---|
| JP | 2003-109775 | 4/2003 |
| JP | 2003-203781 | 7/2003 |
| JP | 2003-203783 | 7/2003 |
| JP | 2003-323987 | 11/2003 |
| JP | 2004-146198 | 5/2004 |
| JP | 2004-152542 | 5/2004 |
| JP | 2004-235152 | 8/2004 |
| JP | 2005-032618 | 2/2005 |
| JP | 2005-530320 | 6/2005 |
| JP | 2005-276542 | 10/2005 |
| JP | 2006-503443 | 1/2006 |
| JP | 2006-147598 | 6/2006 |
| WO | WO/01/39554 | 5/2001 |
| WO | WO/2005/034258 | 4/2005 |
| WO | WO/2005/086541 | 9/2005 |

OTHER PUBLICATIONS

Japanese Office Examination Report issued in connection with related Japanese Patent Application No. 2006-208051 dated Dec. 6, 2011.

Japanese Office Examination Report issued in connection with related Japanese patent application No. 2006-208051 dated Sep. 13, 2011.

\* cited by examiner

*Primary Examiner* — Andrew K Bohaty
(74) *Attorney, Agent, or Firm* — Dentons US LLP

(57) ABSTRACT

An organic light emitting device capable of improving the light extraction characteristics while suppressing the driving voltage and improving the luminescent performance, and a display unit using it are provided. The organic light emitting device includes: a lamination structure that includes a cathode, a plurality of layers including a light emitting layer made of an organic material, and an anode including a metal thin film in this order, in which the cathode is reflective and the anode is semi-transparent to light generated in the light emitting layer; and a resonator structure that resonates the light generated in the light emitting layer between the cathode and the anode.

16 Claims, 4 Drawing Sheets

ORGANIC LIGHT EMITTING DEVICE AND DISPLAY UNIT

CROSS REFERENCES TO RELATED APPLICATIONS

This application is a continuation of U.S. patent application Ser. No. 11/828,746 filed Jul. 26, 2007, the entirety of which is incorporated herein by reference to the extent permitted by law. The present invention contains subject matter related to Japanese Patent Application JP 2006-208051 filed in the Japanese Patent Office on Jul. 31, 2006, the entire contents of which being incorporated herein by reference.

BACKGROUND OF THE INVENTION

1. Field of the Invention

The present invention relates to an organic light emitting device having a light resonator structure and a display unit using the organic light emitting device.

2. Description of the Related Art

In these years, as one of flat panel displays, an organic EL display that displays images by using the organic EL (Electro Luminescence) phenomenon has been noted. Since the organic EL display is a self-luminous type display that displays images by using the foregoing light emitting phenomenon, the organic EL display is superior in terms of the wide view angle, the small power consumption, and the light weight.

The organic EL device mounted on the organic EL display mainly has a structure in which an organic layer is provided between an anode and a cathode. The organic layer includes a light emitting layer as a light emitting source and a hole-transport layer, an electron transport layer and the like for emitting light from the light emitting layer.

Specially, in an active matrix drive system organic EL display unit, the top emission structure capable of maintaining a large aperture ratio of a pixel has been developed (for example, refer to Japanese Unexamined Patent Application Publication Nos. 2003-203781, 2003-203783, 2003-323987, 2004-146198, 2004-152542, 2005-032618, 2005-276542, and 2005-530320). Such a structure is a device structure having a light-reflective lower cathode and a light-transparent upper anode, and different from the structure having a light-transparent lower anode and a light-reflective upper cathode that has been developed in the past. The top emission structure is not affected by lowering of the aperture ratio due to a TFT (Thin Film Transistor) and wiring. Therefore, it is thought that the top emission structure can provide an organic EL display unit with high display performance and superior long-term reliability.

Further, in the top emission structure, as a technique to improve color purity of blue light, green light, and red light, the following technique has been known. In such a technique, in the device structure having a light-reflective lower anode and a light-semi-transparent upper cathode, light generated from the light emitting layer in the organic layer is reflected and resonated (for example, refer to International Publication No. WO 01/039554 and Japanese Unexamined Patent Application Publication No. 10-177896). The device structure of the organic EL device having the light resonant function is generally called "light resonator structure (so-called micro-cavity structure)." In particular, in the organic EL device having the light resonator structure, the light extraction efficiency is improved, that is, the front optical power is increased, and the color purity is improved. Therefore, the organic EL device having the light resonator structure is suitable for a full color display.

SUMMARY OF THE INVENTION

In these days, the practicality of the organic EL display has been widely recognized. Accordingly, improvement of the display performance thereof has been increasingly aspired. However, in the past, the luminescent performance of the organic EL device that affects the display performance has not been sufficient yet, and has left much to be improved.

For example, in the device structure in Japanese Unexamined Patent Application Publication Nos. 2003-203781, 2003-203783, 2003-323987, 2004-146198, 2004-152542, 2005-032618, 2005-276542, and 2005-530320, the technique is based on the premise that an upper anode with the high light transmittance is used. The material of the upper anode is limited to a metal oxide conductor. The metal oxide conductor is generally sputter-deposited. When the metal oxide conductor is directly deposited after the organic layer is formed, the organic layer is largely damaged. Therefore, in the above-mentioned Japanese Unexamined Patent Application Publications, to decrease damage in forming a film, it is considered to use various buffer layers and devise the film forming method. However, the effect thereof is limited, and the reliability and the luminance efficiency decline. In addition, leakage due to sputtered particles is generated. Further, when an additional process is used to decrease the damage, the cost is increased.

In the case of the device structure having the light resonator structure, in general, the optical distance L between the reflective face and the semi-transparent face satisfies Mathematical formula 1.

$$L = (m - \Phi/2\pi)\lambda/2 \qquad \text{Mathematical formula 1}$$

In the formula, L represents the optical distance between the reflective face and the semi-transparent face, m represents an order (0 or a natural number), $\Phi$ represents the sum of the phase shift of the reflected light generated on the reflective face and the phase shift of the reflected light generated on the semi-transparent face (rad), and $\lambda$ represents the peak wavelength of a spectrum of light desired to be extracted from the semi-transparent face side. In Mathematical formula 1, the unit used for L and $\lambda$ may be common, for example, nm is used.

Between the reflective face and the semi-transparent face, there are positions (resonant faces) where the extracted luminescence intensity becomes the maximum. The number of the resonant faces is m+1. When m is 1 or more, the half bandwidth of the emission spectrum is largest in the case that the light emitting face is on the resonant face closest to the reflective face.

In such a light resonator structure, the color purity and the luminescence intensity of the front can be increased. Meanwhile, color shift and intensity lowering to the view angle are observed. As m becomes larger, significant view angle dependency is shown. Considering only the visual field characteristics, m is ideally 0. However, in that case, the organic film thickness becomes thin. Therefore, there is a higher possibility that the light emitting characteristics are affected and a defect due to leak is caused.

To solve the foregoing, for example, it is thought that the following state is effective. That is, for example, m is 1, and the light emitting layer is on the resonant face close to the reflective face.

As a method to arrange the light emitting layer on the resonant face close to the reflective face, the thickness of electron transport layer may be increased, in the existing device structure including the resonant structure typified by International Publication No. WO 01/039554 and Japanese Unexamined Patent Application Publication No. 10-177896, that is, in the existing device in which a light-reflective lower anode, a hole-transport layer, a light emitting layer, an electron transport layer, and a light-semi-transparent upper cathode are layered in this order. However, when the thickness of the electron transport layer made of $Alg_3$ generally used is increased, the driving voltage is extremely increased, leading to increase of the power consumption of the panel.

Meanwhile, in the active matrix organic EL drive system panel, it is increasingly considered to use an amorphous TFT and an organic TFT, in addition to the low temperature polysilicon TFT used from the past. Depending on the structure of the TFT and the design of the drive circuit, the reflective electrode on the substrate side is preferably a cathode in some cases. However, in the existing organic EL display unit having the light resonator structure, only the case that the reflective electrode on the substrate side is an anode is known. Thus, in some cases, it is not able to address diversified active drive circuits.

In view of the foregoing, in the invention, it is desirable to provide an organic light emitting device capable of improving the light extraction characteristics while suppressing the driving voltage and improving the luminescent performance, and a display unit using the organic light emitting device.

According to an embodiment of the invention, there is provided an organic light emitting device including a lamination structure that includes a cathode, a plurality of layers including a light emitting layer made of an organic material, and an anode including a metal thin film in this order, in which the cathode is reflective and the anode is semi-transparent to light generated in the light emitting layer, and a resonator structure that resonates the light generated in the light emitting layer between the cathode and the anode. "Transparent" means that the transmittance of visible light is 10% to 100%. "Reflective" means that the reflectance of visible light is 10% to 100%. "Semi-transparent" means both transparent characteristics and reflective characteristics are included.

According to an embodiment of the invention, there is provided a display unit including a plurality of organic light emitting devices. The plurality of organic light emitting devices are composed of the foregoing organic light emitting devices of the embodiment of the invention.

The organic light emitting device according to the embodiment of the invention has the lamination structure in which the reflective cathode, the plurality of layers including the light emitting layer, and the semi-transparent anode including the metal thin film are layered in this order. Therefore, by increasing the thickness of the layer close to the anode in the plurality of layers, the light emitting layer is arranged on the resonance face close to the cathode where the extraction luminescence intensity is highest in the resonator structure. In the result, lowering of extracted light intensity and shift to the short wavelength side depending on the view angle are suppressed without increasing the driving voltage, and high light extraction efficiency can be obtained.

In the display unit according to the embodiment of the invention, the organic light emitting device according to the embodiment of the invention is used. Therefore, the display performance is improved.

The organic light emitting device according to the embodiment of the invention has the lamination structure in which the reflective cathode, the plurality of layers including the light emitting layer, and the semi-transparent anode including the metal thin film are layered; and the resonator structure including the cathode and the anode. Therefore, the light emitting layer in the resonator structure can be optimally positioned without increasing the driving voltage, the high light extraction characteristics can be realized while the view angle dependency is relaxed, and the luminescent performance can be increased. Further, the display unit according to the embodiment of the invention includes the organic light emitting device of the embodiment of the invention with the high luminescent performance. Therefore, the display performance can be improved. In addition, the display unit according to the embodiment of the invention is extremely suitable for addressing the diversified active drive circuit such as an organic TFT.

Other and further objects, features and advantages of the invention will appear more fully from the following description.

DETAILED DESCRIPTION OF THE PREFERRED EMBODIMENT

An embodiment of the invention will be hereinafter described in detail with reference to the drawings.

First Embodiment

Figure 1:
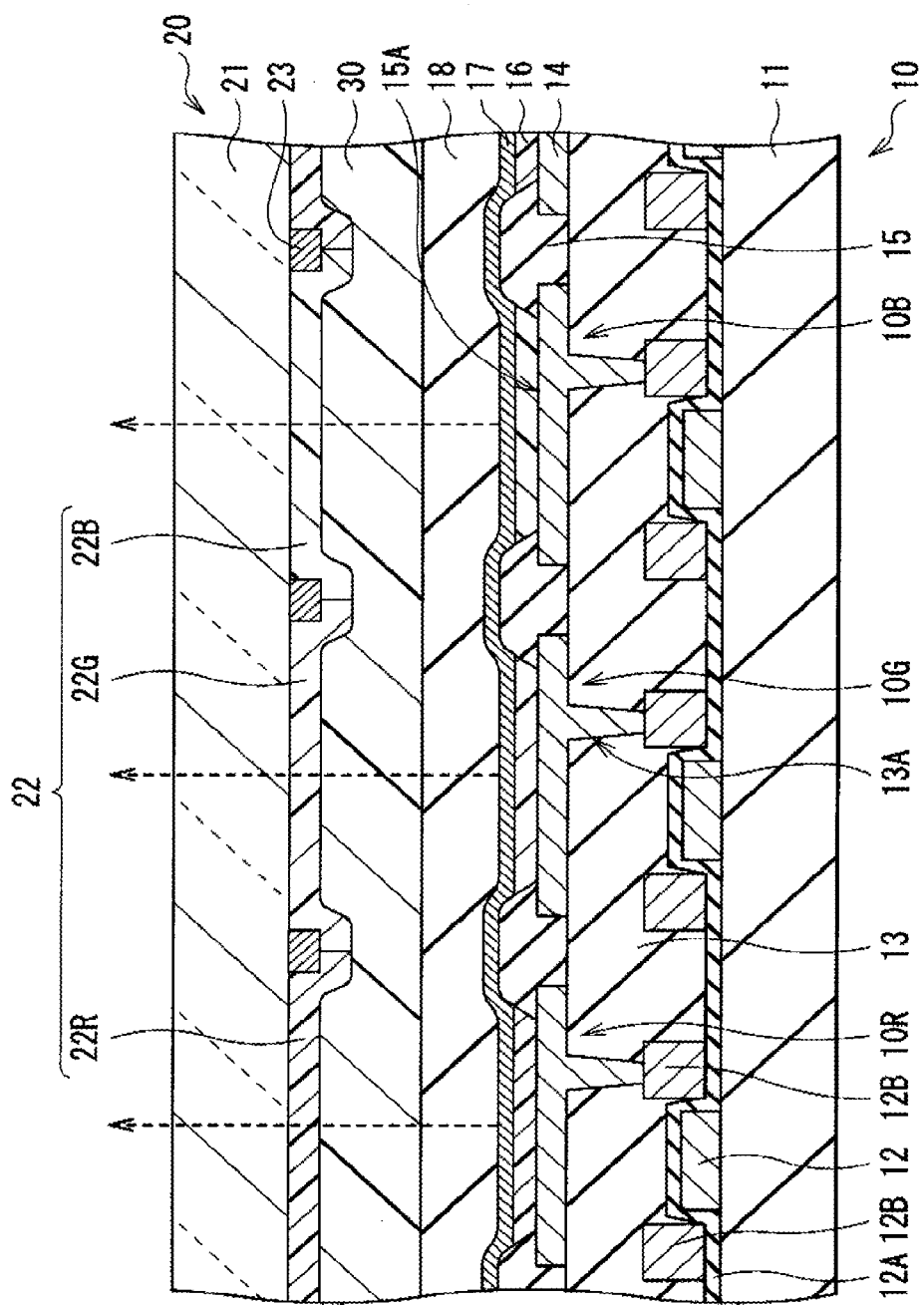
FIG. 1 is a cross section showing a structure of a display unit according to an embodiment of the invention.

FIG. 1 shows a cross sectional structure of an organic EL display unit according to a first embodiment of the invention. The display unit is used as an ultrathin organic light emitting display in which a driving panel 10 and a sealing panel 20 are oppositely arranged, and the whole areas thereof are bonded together by an adhesive layer 30 made of a thermosetting resin or the like. In the driving panel 10, for example, an organic light emitting device 10R for generating red light, an organic light emitting device 10G for generating green light, and an organic light emitting device 10B for generating blue light are sequentially provided in a state of matrix on a driving substrate 11 made of an insulating material such as glass, with a TFT 12 and a planarizing film 13 in between.

The TFT 12 is an active device corresponding to the respective organic light emitting devices 10R, 10G and 10B. The organic light emitting devices 10R, 10G and 10B are driven by active matrix system. A gate electrode (not shown) of the TFT 12 is connected to a not-shown scanning circuit. A source and a drain (either not shown) are connected to a wiring 12B provided with an interlayer insulating film 12A made of, for example, silicon oxide or PSG (Phos-Silicate Glass) in between. The wiring 12B is connected to the source and the drain of the TFT 12 through a not-shown connection hole provided in the interlayer insulating film 12A, and is used as a signal line. The wiring 12B is, for example, about 1.0 μm thick, and is made of, for example, aluminum (Al) or an aluminum (Al)-copper (Cu) alloy. The structure of the TFT 12 is not particularly limited. For example, the structure thereof may be bottom gate type or top gate type.

The planarizing film 13 is a foundation layer for planarizing the surface of the driving substrate 11 formed with the TFT 12 and for uniformalizing the film thickness of each layer of the organic light emitting devices 10R, 10G and 10B. The planarizing film 13 is provided with a connection hole 13A for connecting a cathode 14 of the organic light emitting devices 10R, 10G and 10B to the wiring 12B.

Figure 2:
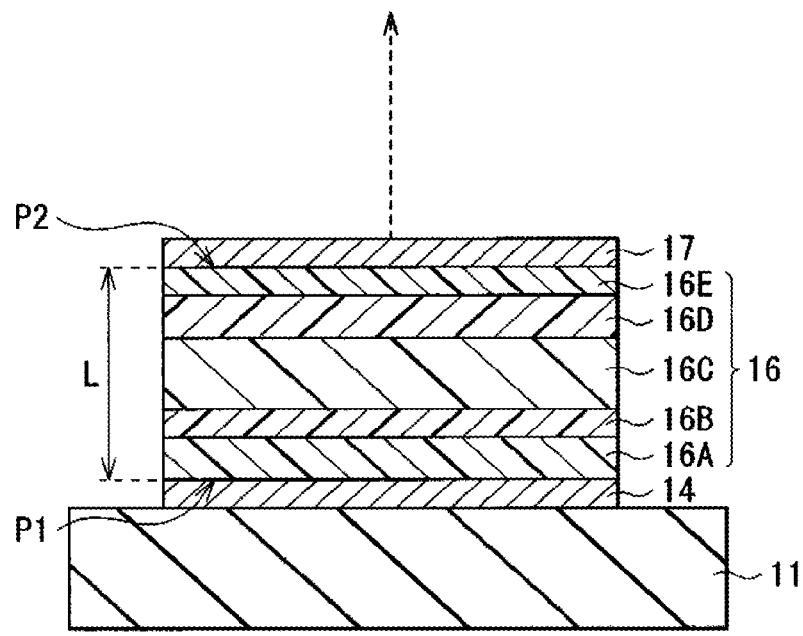
FIG. 2 is a cross section showing a structure of an organic light emitting device shown in FIG. 1.

In the organic light emitting devices 10R, 10G and 10B, for example, a cathode 14, an insulating film 15, a display layer 16 having a plurality of layers including a light emitting layer 16C made of an organic material, and an anode 17 are layered in this order from the driving substrate 11 side with the TFT 12 and the planarizing film 13 in between. In the display layer 16, for example, as shown in FIG. 2, an electron injection layer 16A, an electron transport layer 16B, a light emitting layer 16C, a hole-transport layer 16D, and a hole-injection layer 16E are layered from the cathode 14 side. On the anode 17, a protective layer 18 is formed if necessary.

Further, in the organic light emitting devices 10R, 10G and 10B, the cathode 14 is reflective for light generated in the light emitting layer 16C, while the anode 17 is semi-transparent. The cathode 14 and the anode 17 compose a resonator structure for resonating the light generated in the light emitting layer 16C.

That is, the organic light emitting devices 10R, 10G and 10B have a resonator structure to resonate the light generated in the light emitting layer 16C and extract the light from a second end P2 side, where the end face of the cathode 14 on the light emitting layer 16C side is a first end P1, the end face of the anode 17 on the light emitting layer 16C side is the second end P2, and the display layer 16 is a resonant section. When the organic light emitting devices 10R, 10G and 10B have the resonator structure as above, the light generated in the light emitting layer 16C produces multiple interference and works as a kind of narrow band-pass filter. Thereby, the half bandwidth of the spectrum of the extracted light is reduced, and the color purity can be improved. Outside light entering from the sealing substrate 21 side can be also attenuated by the multiple interference. The reflectance of the outside light in the organic light emitting devices 10R, 10G and 10B can be extremely decreased by combining with a color filter 22 described later, a wave plate, or a polarizing plate (not shown).

To that end, it is preferable that the optical distance L between the first end (reflective face) P1 and the second end (semi-transparent face) P2 of the resonator satisfy Mathematical formula 2, and a resonant wavelength of the resonator (peak wavelength of the spectrum of the extracted light) corresponds with the peak wavelength of the spectrum of the light desired to be extracted.

$$L=(m-\Phi/(2\pi))\lambda/2 \qquad \text{Mathematical formula 2}$$

In the formula, L represents the optical distance between the first end P1 and the second end P2, m represents an order (0 or a natural number), $\Phi$ represents the sum of the phase shift $\Phi_1$ of the reflected light generated at the first end P1 and the phase shift $\Phi_2$ of the reflected light generated at the second end P2 ($\Phi=\Phi_1+\Phi_2$) (rad), and $\lambda$ represents the peak wavelength of the spectrum of the light desired to be extracted from the second end P2 side. In Mathematical formula 2, the unit used for L and $\lambda$ may be common, for example, nm is used.

Between the first end P1 and the second end P2, there are positions (resonant faces) where the extracted luminescence intensity becomes the maximum. The number of such positions is m+1. When m is 1 or more, the half bandwidth of the emission spectrum is largest in the case that the light emitting layer 16C is on the resonant face closest to the first end P1, the lowering of the intensity of the extracted light depending on the view angle is suppressed, and the short wavelength shift of the extracted light is decreased.

Though the order m is not particularly limited, m is preferably 1, that is, two resonant faces exist, and the light emitting layer 16C is arranged on the resonant face close to the first end P1. As described above, as m becomes larger, the view angle dependency is increased. Meanwhile, when m is 0, the thickness of the display layer 16 becomes small, and thus shortcomings of light emitting characteristics such as current leakage easily occur.

As described above, the display unit has the lamination structure in which the cathode 14, the display layer 16 including the light emitting layer 16C, and the anode 17 are layered in this order from the driving substrate 11 side. Thereby, in this display unit, by increasing the thickness of the hole-transport layer 16D, the light emitting layer 16C can be arranged on the resonant face close to the first end P1. Thereby, the light extraction characteristics can be improved without increasing the driving voltage, and the luminescent performance can be improved.

The cathode 14 becoming the first end P1 of the resonator structure desirably has the high reflectance as much as possible, in order to increase the luminance efficiency. Further, since the cathode 14 is an electron injection electrode, an electron injection barrier to the display layer 16 is preferably small, and is desirably made of a metal with the small work function. The thickness of the cathode 14 in the lamination direction (hereinafter simply referred to as thickness) is from 30 nm to 2000 nm, and is made of an alloy of an alkali metal or an alkali earth metal such as lithium (Li), magnesium (Mg), and calcium (Ca); and a metal such as silver (Ag), aluminum (Al), and indium (In). Further, the cathode 14 may have a lamination structure including a layer of the foregoing alkali metal or the foregoing alkali earth metal and a layer of the foregoing metal.

The cathode 14 can be also made of a metal, a metal oxide or the like with the relatively large work function, by using various surface treatments or the after-mentioned electron injection layer 16A. The cathode 14 may have a lamination structure including, for example, a thin film made of a metal with the small work function or a dope layer including a metal with the small work function; and a transparent electrode made of a metal oxide such as tin oxide ($SnO_2$), ITO (Indium tin Oxide), zinc oxide, and titanium oxide.

Meanwhile, the anode 17 as the second end P2 is desirably designed as a semi-transparent reflective layer so that the total of the reflectance and the transmittance is close to 100% as much as possible and the absorptance is small as much as possible in order to decrease loss due to absorption. Further, the anode 17 should function as an electrode, and should have the conductivity sufficient for supplying electron holes to the organic EL device in the thin film as well.

As a material of the anode 17, for example, a metal thin film made of an alloy of an alkali metal or an alkali earth metal such as magnesium (Mg), calcium (Ca) and sodium (Na) and silver (Ag) is preferable. In particular, a metal thin film made of an alloy containing magnesium (Mg) and silver (Ag) is more preferable. The metal thin film made of an alloy containing magnesium (Mg) and silver (Ag) is able to be stably vacuum-deposited, even the thickness of thereof is about 5 nm to 10 nm, the organic EL device can be driven. Therefore, such a metal thin film is suitable as an electrode on the light extraction side in the light resonator structure. The anode 17 made of the alloy of magnesium (Mg) and silver (Ag) is able to be simply formed by a film-forming method that does not damage an organic film much such as resistance heating deposition. In the result, in this case, the defect is decreased and light emission with the high reliability can be obtained, compared to the organic EL device of the related art described in Japanese Unexamined Patent Application Publication Nos. 2003-203781, 2003-203783, 2003-323987, 2004-146198, 2004-152542, 2005-032618, 2005-276542, and 2005-530320. Further, the thickness of the metal thin film of the anode 17 is from 5 nm to about 10 nm or to about 20 nm. Therefore, even when a defect is generated in the display layer 16, there is less possibility that the metal material of the anode 17 intrudes in the defect, and thus a non-light emitting defect due to short circuit can be prevented.

A single metal thin film made of, for example, aluminum (Al), silver (Ag), gold (Au), or copper (Cu) can be used as the anode 17. However, it is difficult to form an ultrathin film with the conductivity capable of driving the organic light emitting devices 10R, 10G and 10B with such a film being about 10 nm thick.

The absorptance α of the metal thin film composing such an anode 17 preferably satisfies Mathematical formula 3, and is more preferably under 40%. Thereby, the resonator structure can be effectively functioned, and the light extraction efficiency can be increased.

$$\alpha(\%)=100-(R+T) \quad \text{Mathematical formula 3}$$

In the formula, α represents the light absorptance (%) in the wavelength region from 400 nm to 800 nm of the metal thin film, R represents the reflectance (%) of the metal thin film to the display layer 16 side, and T represents the transmittance (%) of the metal thin film.

Figure 3:
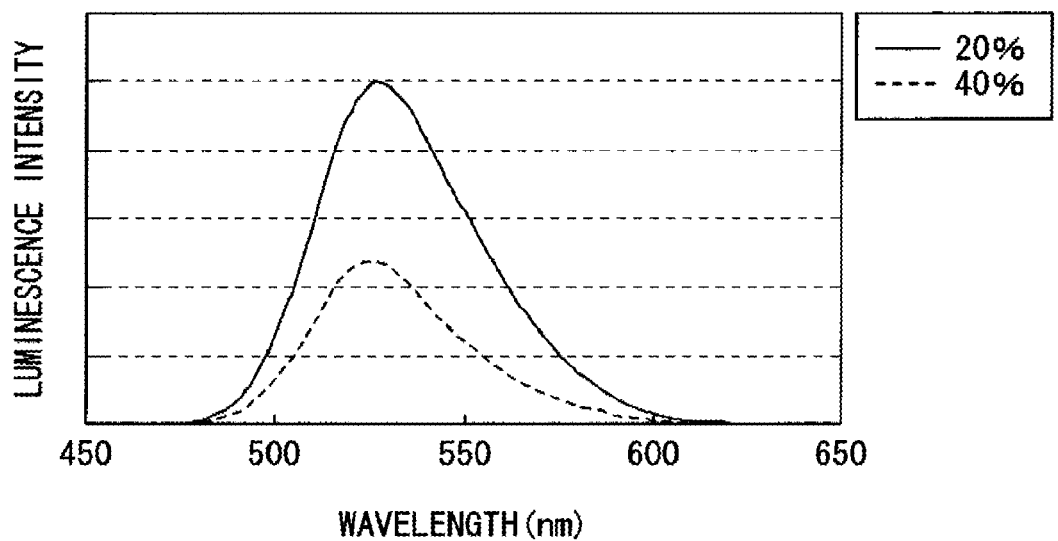
FIG. 3 is a diagram showing a relation between the absorptance of a metal thin film composing an anode and the emission spectrum intensity.

FIG. 3 is a result of calculating the emission spectrums in the case that the absorptance of the metal thin film composing the anode 17 in 550 nm is 20% and 40%. In the case that the absorptance is 20%, the anode 17 is 10 nm thick, and is made of a metal thin film made of an Mg—Ag alloy. As evidenced by FIG. 3, the luminescence intensity in the case that the absorptance is 40% is decreased down to the degree about one half (½) of the case that the absorptance is 20%. That is, when the absorptance of the metal thin film composing the anode 17 is under 40%, the efficiency can be increased, and it is extremely advantageous in order to maintain the display quality.

The insulating film 15 shown in FIG. 1 is intended to secure insulation properties between the cathode 14 and the anode 17, and to accurately obtain a desired form of light emitting regions in the organic light emitting devices 10R, 10G and 10B. The insulating film 15 is made of, for example, a photosensitive resin such as polyimide. The insulating film 15 is provided with an aperture 15A corresponding to the light emitting regions.

The electron injection layer 16A shown in FIG. 2 is intended to increase the electron injection efficiency. The electron transport layer 16B is intended to increase the electron transport efficiency to the light emitting layer 16C. The light emitting layer 16C generates light by electron-hole recombination by applying an electric field. The hole-transport layer 16D is intended to increase the electron hole transport efficiency to the light emitting layer 16C. The hole-injection layer 16E is intended to increase the electron hole injection efficiency. Of the foregoing, layers other than the light emitting layer 16C may be provided if necessary. Further, the display layer 16 may have a different structure according to the light emitting color of the organic light emitting devices 10R, 10G and 10B.

The electron injection layer 16A is preferably made of an alloy of an alkali metal or an alkali earth metal such as lithium (Li), magnesium (Mg), and calcium (Ca) and a metal such as silver (Ag), aluminum (Al), and indium (In), specifically made of an Mg—Ag alloy. Further, the electron injection layer 16A is preferably made of a compound of an alkali metal or an alkali earth metal such as lithium (Li), magnesium (Mg), and calcium (Ca) and halogen such as fluorine and bromine or oxygen, specifically LiF. Further, the electron injection layer 16A may be made of a material in which an alkali metal such as magnesium (Mg) is added to an electron transport organic material such as 8-quinolinole aluminum complex ($Alq_3$). The electron injection layer 16A may have a structure in which two or more of the foregoing films are layered.

When the electron injection layer 16A is made of, for example, a halogenide of an alkali metal such as LiF, a halogenide of an alkali earth metal, an oxide of an alkali metal, or an oxide of an alkali earth metal, the thickness of the electron injection layer 16A is preferably from 0.3 nm to 1.3 nm. Thereby, the driving voltage can be decreased, and the luminance efficiency can be increased.

The electron transport layer 16B is, for example, from 5 nm to 50 nm, and is made of $Alq_3$.

The material of the light emitting layer 16C is different according to the light emitting color of the organic light emitting devices 10R, 10G and 10B. The light emitting layer 16C of the organic light emitting device 10R is, for example, 10 nm to 100 nm thick, and is made of a compound in which volume % of 2,6-bis[4-[N-(4-methoxyphenyl)-N-phenyl]aminostyryl]naphthalene-1,5-dicarbonitrile (BSN-BCN) is mixed with $Alq_3$. The light emitting layer 16C of the organic light emitting device 10G is, for example, 10 nm to 100 nm thick, and is made of a compound in which 3 volume % of coumarine 6 is mixed with $Alq_3$. The light emitting layer 16C of the organic light emitting device 10B is, for example, 10 nm to 100 nm thick, and is made of a compound in which 1 volume % of perylene is mixed with ADN (9,10-di(2-naphthyl)anthracene.

The hole-transport layer 16D is, for example, 5 nm to 300 nm thick, and is made of bis[(N-naphthyl)-N-phenyl]benzidine (α-NPD).

The hole injection layer 16E is preferably, for example, 4 nm thick or more, and is preferably made of the pyrazine derivative shown in Chemical formula 1. In addition, an oxide such as titanium oxide, niobium oxide, molybdenum oxide metal is also preferable. The Mg—Ag alloy composing the anode 17 is generally a material used as an electron injection electrode, and the work function thereof is about 3.7 eV, which is small. The foregoing material is preferably used, since thereby the anode 17 made of the Mg—Ag alloy can function as a hole-injection electrode. Further, the anode 17 made of the Mg—Ag alloy can be prevented from contacting with an organic material composing the display layer 16 to generate chemical change, increasing light absorption, and losing the function as the electrode.

Chemical formula 1

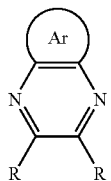

Specially, a hexaazatriphenylene derivative shown in Chemical formula 2 or molybdenum oxide is more preferable. Such materials can be easily formed by resistance heating type vacuum deposition method. In addition, there is no possibility that the conductivity of the anode 17 made of the Mg—Ag alloy is lost due to such materials.

Chemical formula 2

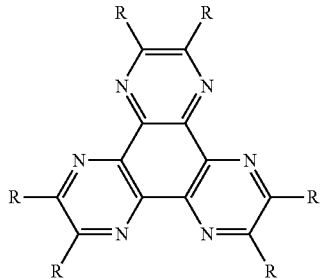

The protective layer 18 is, for example, 500 nm to 10000 nm thick, and is a passivation film made of a transparent derivative. The protective layer 18 is made of, for example, silicon oxide ($SiO_2$), silicon nitride (SiN) or the like.

The sealing panel 20 is located on the anode 17 side of the driving panel 10, and has a sealing substrate 21 that seals the organic light emitting devices 10R, 10G and 10B together with an adhesive layer 30. The sealing substrate 21 is made of a material such as glass transparent to light generated in the organic light emitting devices 10R, 10G and 10B. The sealing substrate 21 is, for example, provided with a color filter 22 and a reflected light absorption film 23 as black matrix. The color filter 22 and the reflected light absorption film 23 extract the light generated in the organic light emitting devices 10R, 10G and 10B, absorb outside light reflected by the organic light emitting devices 10R, 10G and 10B and the wiring therebetween, and improves the contrast.

Though the color filter 22 and the reflected light absorption film 23 may be provided on either side of the sealing substrate 21, the color filter 22 and the reflected light absorption film 23 are preferably provided on the driving panel 10 side. Thereby, the color filter 22 and the reflected light absorption film 23 are not exposed on the surface and can be protected by the adhesive layer 30. The color filter 22 has a red filter 22R, a green filter 22G, and a blue filter 22B. The red filter 22R, the green filter 22G, and the blue filter 22B are sequentially arranged according to the organic light emitting devices 10R, 10G and 10B.

The red filter 22R, the green filter 22G, and the blue filter 22B are, for example, respectively rectangle, and formed with no space therebetween. The red filter 22R, the green filter 22G, and the blue filter 22B are respectively made of a resin mixed with a pigment. The red filter 22R, the green filter 22G, and the blue filter 22B are adjusted so that the light transmittance in the targeted red, green, or blue wavelength band becomes high and the light transmittance in the other wavelength bands becomes low by selecting the pigment.

The reflected light absorption film 23 is provided along the border between the red filter 22R/the green filter 22G/the blue filter 22B. The reflected light absorption film 23 is made of, for example, a black resin film in which a black pigment is mixed therein and the optical density is 1 or more, or a thin film filter using interference of a thin film. Of the foregoing, the black resin film is preferably used, since such a film can be formed inexpensively and easily. In the thin film filter, for example, one or more thin films made of a metal, a metal nitride, or a metal oxide are layered, and light is attenuated by using the interference of the thin films. As the thin film filter, specifically, a lamination in which chromium and chromium oxide (III)($Cr_2O_3$) are alternately layered can be cited.

The display unit can be manufactured, for example, as follows.

First, the reflected light absorption film 23 made of the foregoing material is formed on the sealing substrate 21 made of the foregoing material, and patterned into a given shape. Next, the sealing substrate 21 is coated with a material of the red filter 22R by spin coating or the like, the resultant is patterned by photolithography technique and fired, and thereby the red filter 22R is formed. In patterning, the peripheral edge portion of the red filter 22R preferably covers part of the reflected light absorption film 23. It is difficult to pattern with high precision without covering the reflected light absorption film 23. In addition, the portion of the red filter 22R covering the reflected light absorption film 23 does not affect the image display. Subsequently, in the same manner as in the red filter 22R, the blue filter 22B and the green filter 22G are sequentially formed. Thereby, the sealing panel 20 is formed.

Then, for example, the TFT 12, the interlayer insulating film 12A, and the wiring 12B are formed over the driving substrate 11 made of the foregoing material. The planarizing film 13 made of the foregoing material is formed over the whole area by, for example, spin coat method. Then, the planarizing film 13 is formed into a given shape by providing exposure and development and the connection hole 13A is formed, and fired.

Next, the cathode 14 made of the foregoing material is formed by, for example, sputtering or deposition. Then, etching is made to form the cathode 14 into a given shape.

Subsequently, the whole area of the driving substrate 11 is coated with a photosensitive resin, which is formed by, for example, photolithography method to provide the aperture 15A in the portion corresponding to the cathode 14. The resultant is fired to form the insulating film 15.

After that, corresponding to the aperture 15A of the insulating film 15, the electron injection layer 16A, the electron transport layer 16B, the light emitting layer 16C, the hole-transport layer 16D, the hole-injection layer 16E, and the anode 17 that have the foregoing thickness and are made of the foregoing material are sequentially formed by, for example, deposition to form the organic light emitting devices 10R, 10G and 10B as shown in FIG. 2. Subsequently, the protective layer 18 is formed on the organic light emitting devices 10R, 10G and 10B if necessary. Thereby, the driving panel 10 is formed.

After that, the sealing panel 20 and the driving panel 10 are formed, the adhesive layer 30 made of the foregoing material is formed by coating over the driving substrate 11 on the side where the organic light emitting devices 10R, 10G and 10B are formed. The driving panel 10 and the sealing substrate 20 are bonded to each other with the adhesive layer 30 in between. Consequently, the display unit shown in FIG. 1 is completed.

In the display unit, when a given voltage is applied between the anode 17 and the cathode 14 in the respective organic light emitting devices 10R, 10G and 10B, a current is injected in the light emitting layer 16C, electron-hole recombination occurs, and thereby light is generated. The light is multiply reflected between the anode 17 and the cathode 14, and extracted through the semi-transparent anode 17, the color filter 22, and the sealing substrate 21. In this embodiment, the reflective cathode 14, the display layer 16 including the light emitting layer 16C, and the semi-transparent anode 17 including a metal thin film are sequentially layered in this order. Thereby, by increasing the thickness of the hole-transport layer 16D, the light emitting layer 16C can be arranged on the resonant face close to the cathode 14 in the resonator structure. Therefore, lowering of the intensity of the extracted light and the short wavelength shift depending on the view angle are suppressed. Thus, the light generated in the light emitting layer 16C can be extracted with the high extraction efficiency. Further, selection of the material of the hole-transport layer 16D is more extensive than that of the electron transport material. In addition, the electron hole mobility of the material of the hole-transport layer is relatively higher than the electron mobility of the electron transport material. Therefore, even when the thickness of the hole-transport layer 16D is increased and the light emitting layer 16D is arranged on the resonant face close to the first end P1, the driving voltage hardly rises.

Further, the TFT 12, the wiring 12B and the like that affect the aperture ratio are provided on the reflective cathode 14 side, and thereby the high aperture ratio can be maintained. In addition, by increasing the thickness of the hole-transport layer 16D, coating effect on the substrate by the organic film of the display layer 16 is increased, and thus a defect resulting from defective film-forming on the cathode 14, attachment of foreign matters thereon and the like, and short circuit resulting from loss of the organic film are prevented.

Meanwhile, in the past, the light-reflective anode, the hole-transport layer, the light emitting layer, the electron transport layer, and the light-semi-transparent cathode are layered in this order over the substrate. Therefore, to arrange the light emitting layer on the resonant face close to the anode, the electron transport layer is thickened. In the result, the driving voltage is significantly increased, leading to increase of the power consumption of the panel.

As above, in this embodiment, in the organic light emitting devices 10R, 10G and 10B having a resonator structure, the reflective cathode 14, the display layer 16 including the light emitting layer 16C, and the semi-transparent anode 17 are layered in this order. Therefore, it is possible to suppress the view angle dependency without increasing the driving voltage, improve the light extraction characteristics, and improve the luminescent performance. In the result, the display unit including the organic light emitting devices 10R, 10G and 10B with the high luminescent performance can improve the display performance. In particular, the display unit in this embodiment is extremely suitable for a case using an organic TFT or the like as the TFT 12.

Further, the thickness of the hole-transport layer 16D can be increased. Therefore, defects due to short circuit can be decreased, and the reliability can be improved.

Further, the TFT 12, the wiring 12B and the like that affect the aperture ratio are provided on the reflective cathode 14 side, and thereby the high aperture ratio can be maintained.

EXAMPLES

Further, specific examples of the invention will be described in detail.

Examples 1-1 and 1-2

The organic light emitting devices 10B were formed in the same manner as in the foregoing embodiment.

First, the cathode 14 made of an aluminum-neodymium alloy being 100 nm thick was formed over the driving substrate 11 made of glass. Next, the insulating film 15 made of the foregoing organic insulating material was formed. The insulating film 15 was patterned and thereby the aperture 15A of 2 mm×2 mm was provided corresponding to the light emitting region to expose the cathode 14.

Subsequently, the metal mask having the aperture corresponding to the exposed portion of the cathode 14 was arranged in the vicinity of the driving substrate 11. With the use of vacuum vapor deposition method under the vacuum of $10^{-4}$ Pa or less, a co-vapor deposition film of magnesium (Mg) and silver (Ag) (Mg:Ag=10:1) being 2 nm thick and a LiF film being 0.3 nm thick were layered to form the electron injection layer 16A.

After that, with the use of vacuum vapor deposition method again, the electron transport layer 16B, the light emitting layer 16C, the hole-transport layer 16D, and the electron injection layer 16E that were made of the foregoing material were sequentially formed, and thereby the display layer 16 was formed. At that time, as a material of the hole-injection layer 16E, the hexaazatriphenylene derivative shown in Chemical formula 2 was used in Example 1-1, and molybdenum oxide was used in Example 1-2. The thickness of each layer was set so that the optical distance L between the cathode 14 and the anode 17 satisfied Mathematical formula 2, and the blue light emission was amplified by the resonator structure. That is, the electron transport layer 16B was 20 nm thick, the light emitting layer 16C was 25 nm thick, the hole-transport layer 16D was 130 nm thick, and the hole-injection layer 16E was 8 nm thick.

After the display layer 16 was formed, with the use of vacuum vapor deposition method again, as the anode 17, a co-vapor deposition film of magnesium (Mg) and silver (Ag) (Mg:Ag=10:1) being 10 nm thick was formed. Consequently, the organic light emitting device 10B shown in FIG. 2 was obtained.

Further, a film made of the hexaazatriphenylene derivative shown in Chemical formula 2 being 8 nm thick and an Mg—Ag alloy film (Mg:Ag=10:1) being 10 nm thick were sequentially layered over a quartz glass plate, and the transmittance and the reflectance in the wavelength of 550 nm were examined. In the result, semi-transparent characteristics with the transmittance of 41% and the reflectance of 39% were observed. For molybdenum oxide, examination was made similarly. That is, a film made of molybdenum oxide being 8 nm thick and an Mg—Ag alloy film (Mg:Ag=10:1) being 10 nm thick were sequentially layered over a quartz glass plate, and the transmittance and the reflectance in the wavelength of 550 nm were examined. In the result, semi-transparent characteristics with the transmittance of 46% and the reflectance of 23% were observed.

Figure 4:
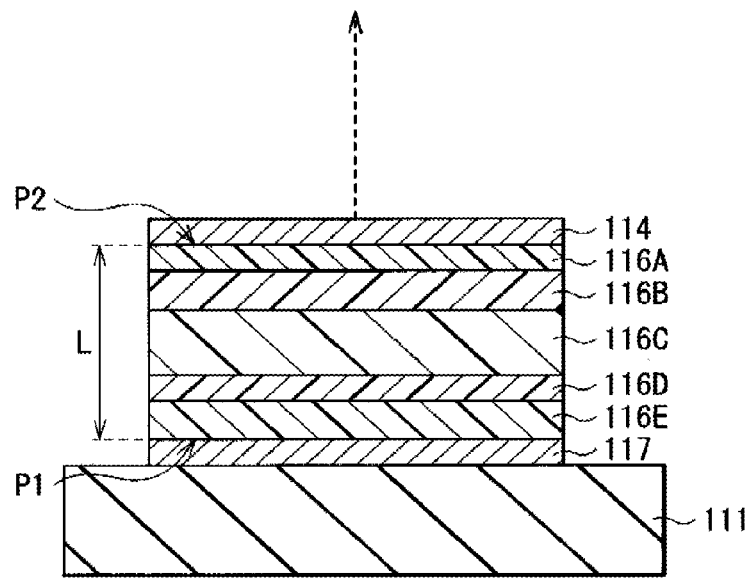
FIG. 4 is a cross section showing a structure of an organic light emitting device formed in a comparative example of the invention.

As Comparative example 1, an organic light emitting device that has the existing top emission structure in which a reflective anode 117, an electron injection layer 116E, a hole-transport layer 116D, a light emitting layer 116C, an electron transport layer 116B, an electron injection layer 116A, and a semi-transparent cathode 114 are layered in this order from a driving substrate 111 side as shown in FIG. 4, and that generates blue light was formed.

That is, the anode 117 made of an aluminum-neodymium alloy being 100 nm thick was formed over the driving substrate 111 made of glass. Next, an insulating film (not shown) was formed in the same manner as in Examples 1-1 and 1-2. Subsequently, the hole-injection layer 116E made of the hexaazatriphenylene derivative shown in Chemical formula 2, the hole-transport layer 116D made of α-NPD, the light emitting layer 116C made of a material similar to that of Example 1-1, the electron transport layer 116B made of $Alq_3$, and the electron injection layer 116A made of LiF were sequentially formed. The thickness of each layer was set so that the optical distance L between the anode 117 and the cathode 114 satisfied Mathematical formula 2, and the blue light emission was amplified by the resonator structure. That is, the hole-injection layer 116E was 8 nm thick, the hole-transport layer 116D was 140 nm thick, the light emitting layer 116C was 25 nm thick, the electron transport layer 116B was 20 nm thick, and the electron injection layer 116A was 0.3 nm thick. After that, the cathode 114 made of a co-vapor deposition film of magnesium (Mg) and silver (Ag) (Mg:Ag=10:1) being 10 nm thick was formed.

For the obtained organic light emitting devices of Examples 1-1, 1-2 and Comparative example 1, the current density-voltage characteristics and the emission spectrums where the current density was 10 $mA/cm^2$ were examined. The results are shown in FIG. 5 and FIG. 6.

Figure 5:
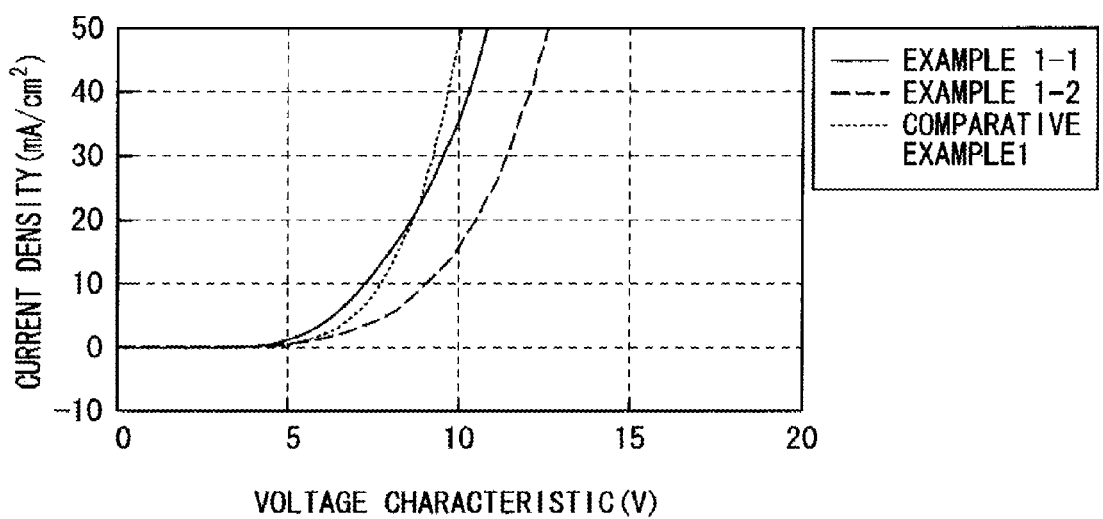
FIG. 5 is a diagram showing results of examples of the invention.
Figure 6:
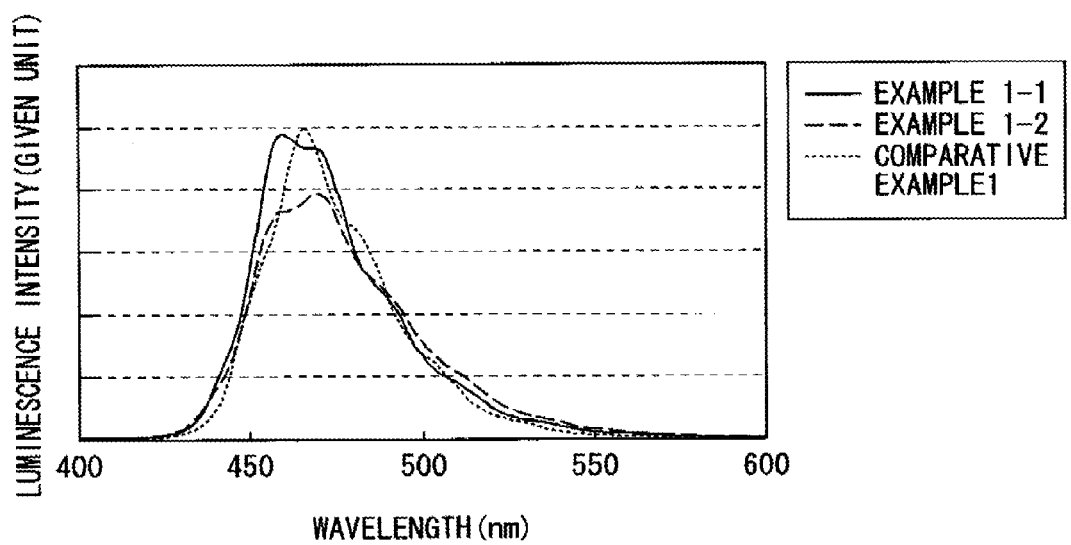
FIG. 6 is a diagram showing results of the examples of the invention.

As evidenced by FIG. 5 and FIG. 6, in Examples 1-1 and 1-2, the electron hole injection characteristics and the luminescence intensity were preferable almost equally to those of Comparative example 1, and the driving voltage was not increased. That is, it was found that in the organic light emitting device 10B having the resonator structure, when the reflective cathode 14, the display layer 16 including the light emitting layer 16C, and the semi-transparent anode 17 were layered in this order, the organic light emitting device 10B with the superior light extraction characteristics and the high luminescent performance can be realized without increasing the driving voltage.

Further, in Example 1-1, both the electron hole injection characteristics and the luminescence intensity were more preferable than in Example 1-2. That is, it was found that when the hole-injection layer 16E was made of the hexaazatriphenylene derivative shown in Chemical formula 2, the electron hole injection characteristics and the luminescence intensity could be more improved.

Examples 2-1 to 2-4

The organic light emitting devices 10B were formed in the same manner as in Example 1-1, except that the thickness of the hole-injection layer 16E was changed as shown in Table 1. For the obtained organic light emitting devices 10B of Examples 2-1 to 2-4, the driving voltage and the luminance efficiency at the current density of 10 $mA/cm^2$ were examined. The results are shown in Table 1 together.

TABLE 1

|  | Thickness of hole-injection layer (nm) | Driving voltage at 10 $mA/cm^2$ (V) | Luminance efficiency at 10 $mA/cm^2$ (cd/A) |
| --- | --- | --- | --- |
| Example 2-1 | 2 | 19.9 | 0.14 |
| Example 2-2 | 3 | 20.0 | 1.06 |

TABLE 1-continued

|  | Thickness of hole-injection layer (nm) | Driving voltage at 10 $mA/cm^2$ (V) | Luminance efficiency at 10 $mA/cm^2$ (cd/A) |
| --- | --- | --- | --- |
| Example 2-3 | 4 | 6.3 | 5.77 |
| Example 2-4 | 8 | 5.2 | 5.16 |

As evidenced by Table 1, in Examples 2-3 and 2-4 in which the thickness of the hole-injection layer 16E was 4 nm and 8 nm, the driving voltage was lower and the luminance efficiency was higher than in Examples 2-1 and 2-2 in which the thickness of the hole-injection layer 16E was 2 nm and 3 nm. That is, it was found that when the thickness of the hole-injection layer 16E was 4 nm or more, high luminance efficiency could be obtained with the lower driving voltage.

Examples 3-1 to 3-8

The organic light emitting devices 10B were formed in the same manner as in Example 1-1, except that the thickness of the LiF film of the electron injection layer 16A was changed as shown in Table 2. For the obtained organic light emitting devices 10B of Examples 3-1 to 3-8, the driving voltage and the luminance efficiency at the current density of 10 $mA/cm^2$ were examined. The results are shown in Table 2 together.

TABLE 2

|  | Thickness of LiF film (nm) | Driving voltage at 10 $mA/cm^2$ (V) | Luminance efficiency at 10 $mA/cm^2$ (cd/A) |
| --- | --- | --- | --- |
| Example 3-1 | 0 | 7.6 | 4.35 |
| Example 3-2 | 0.3 | 6.1 | 5.19 |
| Example 3-3 | 0.6 | 5.3 | 5.12 |
| Example 3-4 | 1.0 | 6.2 | 5.15 |
| Example 3-5 | 1.3 | 6.2 | 5.24 |
| Example 3-6 | 1.6 | 6.7 | 5.06 |
| Example 3-7 | 2.0 | 6.7 | 4.71 |
| Example 3-8 | 2.5 | 7.1 | 4.62 |

As evidenced by Table 2, in Examples 3-2, 3-3, 3-4, and 3-5 in which the thickness of the LiF film of the electron injection layer 16A was 0.3 nm, 0.6 nm, 1.0 nm, and 1.3 nm, respectively, the driving voltage was lower and the luminance efficiency was higher than in Example 3-1 in which the thickness of the LiF film of the electron injection layer 16A was 0 nm and in Examples 3-6, 3-7, and 3-8 in which the thickness of the LiF film of the electron injection layer 16A was 1.6 nm, 2.0 nm, and 2.5 nm, respectively. In particular, in Example 3-3 in which the thickness of the LiF film of the electron injection layer 16A was 0.6 nm, the driving voltage was the minimum, which was preferable in terms of reduction in the power consumption as well. In a general device structure in which the anode, the display layer including a light emitting layer, and the cathode are layered in this order from the driving substrate side (refer to Comparative example 1), the thickness of the electron injection layer made of LiF is most preferably about 0.3 nm. Meanwhile, in these examples, since the cathode 14, the display layer 16, and the anode 17 are layered in this order from the driving substrate 11 side, diffusion of LiF into the electron transport layer 16B made of $Alq_3$ was small. Therefore, it is thought that increasing the thickness of the LiF film in the electron injection layer 16A more than in the general structure was appropriate in order to improve the electron injection characteristics.

That is, it was found that when the thickness of the LiF film of the electron injection layer 16A was 0.3 nm to 1.3 nm, high luminance efficiency could be obtained with the lower driving voltage. It is expected that not only in the case of using LiF, but also in the case of using a halogenide of other alkali metal, a halogenide of an alkali earth metal, an oxide of an alkali metal, or an oxide of an alkali earth metal, effects similar to those of these examples may be obtained.

Examples 4-1 to 4-5

The organic light emitting devices 10B were formed in the same manner as in Example 1-1, except that the structure of the electron injection layer 16A was different from that of Example 1-1. That is, in Example 4-1, the electron injection layer 16A was made of a LiF film being 0.6 nm thick. In Example 4-2, the electron injection layer 16A had a structure in which an Mg—Ag alloy film being 2 nm thick and a LiF film being 0.6 nm thick were layered in this order from the cathode 14 side. In Example 4-3, the electron injection layer 16A had a structure in which an Mg—Ag alloy film being 2 nm thick, a LiF film being 0.6 nm thick, and a mixed film in which 5 volume % of magnesium (Mg) was added to $Alq_3$ being 5 nm thick were layered in this order from the cathode 14 side. In Example 4-4, the electron injection layer 16A had a structure in which an Mg—Ag alloy film being 2 nm thick, a mixed film in which 5 volume % of magnesium (Mg) was added to $Alq_3$ being 5 nm thick, and a LiF film being 0.6 nm thick were layered in this order from the cathode 14 side. In Example 4-5, the electron injection layer 16A had a structure in which an Mg—Ag alloy film being 2 nm thick and a mixed film in which 5 volume % of magnesium (Mg) was added to $Alq_3$ being 5 nm thick were layered in this order from the cathode 14 side. The thickness of the electron transport layer 16B was 20 nm in Examples 4-1 and 4-2, and 15 nm in Examples 4-3 to 4-5.

For the obtained organic light emitting devices 10B of Examples 4-1 to 4-5, the driving voltage and the luminance efficiency at the current density of 10 mA/cm$^2$ were examined. The results are shown in Table 3 together.

TABLE 3

|  | Structure of electron injection layer | Driving voltage at 10 mA/cm$^2$ (V) | Luminance efficiency at 10 mA/cm$^2$ (cd/A) |
|---|---|---|---|
| Example 4-1 | LiF 0.6 nm | 13.1 | 2.44 |
| Example 4-2 | Mg—Ag 2 nm/LiF 0.6 nm | 6.5 | 4.70 |
| Example 4-3 | Mg—Ag 2 nm/LiF 0.6 nm/ $Alq_3$ + Mg (5%) 5 nm | 5.2 | 4.53 |
| Example 4-4 | Mg—Ag 2 nm/$Alq_3$ + Mg (5%) 5 nm/LiF 0.6 nm | 5.1 | 4.22 |
| Example 4-5 | Mg—Ag 2 nm/$Alq_3$ + Mg (5%) 5 nm | 6.8 | 3.53 |

As evidenced by Table 3, in Examples 4-2 to 4-5 in which the electron injection layer 16A had a lamination structure including the Mg—Ag alloy film, the driving voltage was lower and the luminance efficiency was higher than in Example 4-1 in which the electron injection layer 16A was made of only the LiF film and did not include the Mg—Ag alloy film. In particular, in Examples 4-3 and 4-4 in which the electron injection layer 16A had the lamination structure including the Mg—Ag alloy film, the mixed film in which 5 volume % of magnesium (Mg) was added to $Alq_3$, and the LiF film, both the driving voltage and the luminance efficiency were favorable. That is, it was found that when the electron injection layer 16A was made of the Mg—Ag alloy, high luminance efficiency could be obtained with the lower driving voltage. In addition, it was found that when the electron injection layer 16A was made of a material in which 5 volume % of magnesium (Mg) was added to $Alq_3$, high luminance efficiency could be obtained with the further lower driving voltage.

While the invention has been described with reference to the embodiment and the examples, the invention is not limited to the foregoing embodiment and the foregoing examples, and various modifications may be made. For example, the material, the thickness, the film-forming method, the film-forming conditions and the like of each layer are not limited to those described in the foregoing embodiment, but other material, other thickness, other film-forming method, and other film-forming conditions may be adopted. For example, the driving substrate 11 may be made of silicon (Si) or a plastic instead of glass. Further, the driving substrate 11 is not necessarily the TFT substrate.

Further, the invention is not limited to the active matrix drive system display unit, but can be also applied to the simple matrix drive system display unit.

In addition, in the foregoing embodiment and the foregoing examples, the structure of the organic light emitting devices 10R, 10G and 10B has been specifically described. However it is not necessary to provide all layers such as the protective layer 18, and other layer may be further provided. For example, the cathode 14 can have two-layer structure in which an transparent conductive film is layered on a dielectric multilayer film or a reflective film such as Al. In this case, the end face of the reflective film on the light emitting layer side forms the end of a resonant section, and the transparent conductive film forms part of the resonant section.

Further, in the foregoing embodiment and the foregoing examples, the description has been given of the case that the organic light emitting devices 10R, 10G and 10B have the resonator structure to resonate the light generated in the light emitting layer 16C and extract the light from the second end P2 side, where the end face of the cathode 14 on the light emitting layer 16C side is the first end P1, the end face of the anode 17 on the light emitting layer 16C side is the second end P2, and the display layer 16 is the resonant section. However, the first end P1 and the second end P2 may be formed on the interface between layers made of two types of materials with the refractive index different from each other. For example, in the foregoing embodiment and the foregoing examples, the description has been given of the case that the anode 17 is made of the semi-transparent metal thin film. However, the anode 17 may have a structure in which a semi-transparent metal thin film and a transparent electrode are sequentially layered from the anode 14 side. The transparent electrode is intended to decrease the electric resistance of the semi-transparent metal thin film, and is made of a conductive material having translucency sufficient for the light generated in the light emitting layer. As a material of the transparent electrode, for example, ITO, or a compound containing indium, zinc (Zn), and oxygen is preferable. Thereby, even when film forming is made at the room temperatures, favorable conductivity can be obtained. The thickness of the transparent electrode can be, for example, from 30 nm to 1000 nm. In this case, a resonator structure in which the semi-transparent metal thin film is used as one end, the other end is provided in the position facing the semi-transparent metal thin film with the transparent electrode in between, and the transparent electrode is used as a resonant section. Further, it is preferable that such a resonator structure is provided, the organic light emitting devices 10R, 10G and 10B are covered with a protective film, and the protective film is made of a material having the refractive index almost the same as that of the material of the transparent electrode. Thus, the protective film can become part of the resonant section.

In addition, the invention can be also applied to a case in which the anode 17 is composed of a transparent electrode, the reflectance of the end face of the transparent electrode on the opposite side of the display layer 16 is large, and a resonator structure in which the end face of the cathode 14 on the light emitting layer 16C side is the first end, and the end face of the transparent electrode on the opposite side of the display layer 16 is the second end. For example, it is possible that the transparent electrode is contacted with the air layer, the reflectance of the interface between the transparent electrode and the air layer is large, and the interface is used as the second end. Otherwise, it is possible that the reflectance of the interface with the adhesive layer is large, and the interface is used as the second end. Otherwise, it is possible that the organic light emitting devices 10R, 10G and 10B are covered with a protective film, the reflectance of the interface with the protective layer is large, and the interface is used as the second end.

It should be understood by those skilled in the art that various modifications, combinations, sub-combinations and alternations may occur depending on design requirements and other factors insofar as they are within the scope of the appended claims or the equivalents thereof.

What is claimed is:

1. An organic light emitting device on a substrate comprising:
    a lamination structure that includes, in this order,
        (a) a lower electrode,
        (b) a light emitting layer made of an organic material,
        (c) an upper electrode including a metal thin film, and
        (d) a protective layer; and
    a resonator structure between the lower electrode and the upper electrode configured to resonate the light generated in the light emitting layer such that the light is emitted through the upper electrode,
    wherein,
        the lower electrode comprises silver,
        the thickness of the lower electrode is from 30 nm to 2000 nm,
        the upper electrode comprises a magnesium-silver alloy,
        the thickness of the upper electrode is from 5 nm to 20 nm,
        the protective layer comprises silicon oxide or silicon nitride, and
        the thickness of the protective layer is from 500 nm to 10000 nm.

2. The organic light emitting device according to claim 1, wherein the plurality of layers further includes a hole injection layer, wherein the upper electrode is disposed above the hole injection layer such that the upper electrode is in contact with the hole injection layer.

3. The organic light emitting device according to claim 1, wherein:
    the plurality of layers further includes an electron transport layer and an electron injection layer, and
    the electron injection layer is disposed between the electron transport layer and the lower electrode.

4. The organic light emitting device according to claim 3, wherein a thickness of the electron transport layer is greater than a thickness of the electron injection layer.

5. The organic light emitting device according to claim 1, wherein:
    the plurality of layers further includes an electron injection layer, and
    the electron injection layer is a laminate structure that includes a first film comprising a magnesium-silver alloy and a second film comprising an alkali metal or an alkali earth metal.

6. The organic light emitting device according to claim 1, wherein the light emitting layer is closer in distance to the lower electrode than the upper electrode in a thickness direction.

7. The organic light emitting device according to claim 2, wherein the hole injection layer is made of a metal oxide.

8. The organic light emitting device according to claim 1, wherein:
    the plurality of layers further includes a hole transport layer and an electron transport layer, and
    an electron mobility of the hole transport layer is relatively higher than an electron mobility of the electron transport layer.

9. The organic light emitting device according to claim 1, wherein the substrate is a driving substrate that includes a transistor.

10. The organic light emitting device according to claim 2, wherein a thickness of the hole injection layer is at least 4 nm.

11. The organic light emitting device according to claim 2, wherein the thickness of the hole injection layer is not greater than 8 nm.

12. The organic light emitting device according to claim 1, wherein the lower electrode is a cathode and the upper electrode is an anode.

13. The organic light emitting device according to claim 1, wherein a ratio of Mg:Ag in the upper electrode is about 10:1.

14. The organic light emitting device according to claim 1, wherein the thickness of the upper electrode is from 5 nm to about 10 nm.

15. The organic light emitting device according to claim 14, wherein the thickness of the upper electrode is about 10 nm.

16. A display unit including the organic light emitting device according to claim 1.

* * * * *